United States Patent [19]

Cordi et al.

[11] Patent Number: 5,141,960
[45] Date of Patent: Aug. 25, 1992

[54] TRICYCLIC GLYCINAMIDE DERIVATIVES AS ANTI-CONVULSANTS

[75] Inventors: Alexis A. Cordi, St. Louis, Mo.; Claude L. Gillet, Blanmont, Belgium

[73] Assignee: G. D. Searle & Co., Chicago, Ill.

[21] Appl. No.: 720,337

[22] Filed: Jun. 25, 1991

[51] Int. Cl.⁵ .................. A61K 31/165; C07C 237/14
[52] U.S. Cl. .................. 514/619; 514/227.5;
514/237.5; 514/255; 514/325; 514/423;
514/616; 514/617; 514/618; 514/620; 544/58.4;
544/154; 544/155; 544/380; 546/195; 548/528;
564/153; 564/154; 564/156; 564/162; 564/163;
564/166; 564/167; 564/168
[58] Field of Search .............. 564/153, 154, 156, 162,
564/163, 166, 167, 168; 544/58.4, 154, 155, 380;
546/195; 548/528; 514/227.5, 237.5, 255, 325,
423, 616, 617, 618, 619, 620

[56] References Cited

U.S. PATENT DOCUMENTS 3,821,249  6/1974  Malen et al. .................. 260/327
4,025,651  5/1977  Kirino et al. .................. 424/320
4,267,344  5/1981  Halstrom et al. .................. 548/227
4,639,468  1/1987  Roncucci et al. .................. 514/620

FOREIGN PATENT DOCUMENTS 636245   9/1962  Belgium .
706262   5/1968  Belgium .
498661   5/1930  Fed. Rep. of Germany .
1181673  2/1970  United Kingdom .

OTHER PUBLICATIONS

R. M. Peck et al, *J. Med. Chem.*, 19(12), 1422–1423 (1976).

B. Wysocka-Skrzela, *Pol. J. Chem.*, 56(10–12), 1573–1576 (1982).
J. Pless, *Helv. Chim. Acta.*, 59, Fasc. 2, Nr. 53, 499–512 (1976).
B. Gaugain, *Biochem.*, 20, 3035–3042 (1981).
V. A. Shibnev et al, *Bioorg. Khim.*, 10(7), 921–926 (1984).

*Primary Examiner*—Richard L. Raymond
*Attorney, Agent, or Firm*—J. Timothy Keane; Charles E. Smith; Paul D. Matukaitis

[57] ABSTRACT

A class of tricyclic glycinamide derivatives is described having use in treatment of CNS dysfunctions such as epilepsy and convulsive disorders. Compounds of most interest are those of the formula

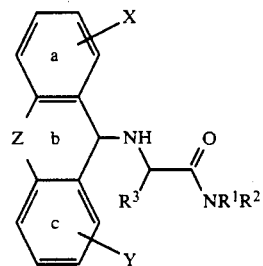

wherein each of X and Y is hydrido; wherein Z is selected from methylene, ethylene, ethenylene, thiomethylene and thioethylene; and wherein each of $R^1$, $R^2$ and $R^3$ is hydrido; or a pharmaceutically-acceptable salt thereof.

6 Claims, No Drawings

TRICYCLIC GLYCINAMIDE DERIVATIVES AS ANTI-CONVULSANTS

FIELD OF THE INVENTION

This invention is in the field of clinical neurology and relates to a class of compounds, compositions and methods useful for treatment of Central Nervous System (CNS) dysfunctions. Of particular interest is a class of tricyclic glycinamide compounds for use as anti-convulsants and in management of epilepsy.

BACKGROUND OF THE INVENTION

Convulsive disturbances are typically observed in humans as rapidly alternating contractions and relaxations of muscles which are manifested by irregular movements of the limbs or body and typically accompanied by unconsciousness. The most common cause of convulsions in human adults is epilepsy. Convulsive seizures occur in children from a variety of causes. Convulsions in children may be due to brain damage from birth injuries, or due to dietary deficiencies such as a lack of vitamin D, or due to metabolic disorders such as hypoglycemia or hypokalemia, or due to a sudden body temperature elevation caused by infections such as pneumonia. Convulsions may also be initiated by brain diseases such as meningitis, encephalitis or tumors, and also by conditions brought on by asphyxia or skull fracture.

Tricyclic compounds have been investigated for various CNS uses. For example, Belgian Patent No. 706,262 describes a class of diphenylenemethane amine and amide derivatives mentioned for use as anti-convulsants, as well as for anti-depressive, anti-inflammatory and analgesic uses, and mentions in particular the compound 2-[fluorene-9-yl)amino]acetamide. U.S. Pat. No. 3,821,249 described a series of dibenzothiazepin derivatives asserted to possess psychostimulant, anti-depressive, analgesic, anti-tussive, anti-histaminic and gastric anti-secretory properties, such series including certain specific 7-[dibenzo(a,d)cycloheptadien-5-yl] aminoheptanoic acid derivatives and certain specific 7-[chlorodibenzo(b,e)thiepin-11-yl]aminoheptanoic acid derivatives.

Various tricyclic compounds have been investigated for other pharmaceutical uses. For example, German Patent No. 498,661 describes synthesis of a series of nitro-9-aminoacridine derivatives which are mentioned for use as bacteriostatics. U.K. Patent No. 1,181,673 describes a series of xanthen and thiaxanthen urea derivatives having utility in treatment of peptic ulceration. Carcinogenicity studies have been carried out involving a family of N-(9-acridinyl)glycylglycylglycine compounds [R. M. Peck et al, *J. Med. Chem.*, 19(12), 1422-1423 (1976)]. A family of acridinylglycine derivatives has been reported to have tumor-inhibiting properties [B. Wysocka-Skrzela, *Pol. J. Chem.*, 56(10-12), 1573-1576 (1982)].

Tricyclic derivatives have been described as intermediates or end products of various laboratory-scale synthetic methods, without mention of pharmaceutical utility. Derivatives of the 10,11-dihydro-5H-dibenzo[a,d]cyclohepten-5-yl group (also known as 5-dibenzosuberyl group) have been identified as protecting groups in amine synthesis with specific mention of the compound 2-(2,3-6,7-dibenzocycloheptanylamino)acetic acid [J. Pless, *Helv. Chim. Acta.*, 59, Fasc. 2, Nr. 53, 499-512 (1976)]. A family of 2-methoxy-6-chloro-9aminoacridine derivatives bearing a carboxamide side chain have been studied as RNA intercalating probes, an example of one specific compound being 2-(2-methoxy-6-chloroacridine-9-aminoacetamide [B. Gaugain, *Biochem.*, 20, 3035-3042 (1981)]. U.S. Pat. No. 4,267,344 describes a series of N-substituted-N-carboxyanhydrides of α-amino acids for use in synthesis of peptides. Certain 2-methoxy-6-chloro-9-acridinylglycnie derivatives have been used as fluorescent groups for attachment to peptides for analytical purposes [V. A. Shibnev et al, *Bioorg. Khim.*, 10(7), 921-926 (1984)].

Glycinamide-type compounds in general have been described or various purposes. For example, German Patent No. 2,511,311 describes a family of glycinamides for use as fungicides. Belgian Patent No. 636,245 describes a family of 2-(ω-alkoxycarbonylalkylideneamino)acetamide compounds asserted to have pharmaceutical properties. U.S. Pat. No. 4,639,468 describes a class of 2-amino-acetamide derivatives having use in treatment of epilepsy, dyskinesia such as Parkinsonism, memory troubles and psychic disorders such as depression.

DESCRIPTION OF THE INVENTION

Treatment of mammal afflicted with or susceptible to a CNS disorder, such as epilepsy, convulsions, dyskinesia, cognitive disorder or other neurodegenerative disease or neurotoxic injury, is provided by administering to the mammal a therapeutically-effective amount of a compound selected from a class of tricyclic glycinamide compounds defined by Formula I:

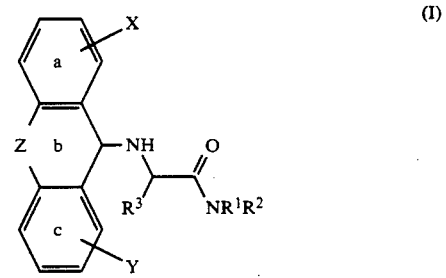

wherein each of X and Y is independently selected from hydrido, hydroxyl, alkyl, haloalkyl, halo, alkoxy, alkylthio, alkylsulfinyl, alkylsulfonyl, nitro, amino and alkylamino; wherein Z is a single bond so that the b ring is a five membered ring, or Z is a group selected from alkylene, alkenylene, carbonyl, carbonylalkylene, oxygen atom, imino (i.e., —NH—), iminoalkylene, iminoalkylidene, aminoalkylene, sulfur atom, thioalkylene, sulfinyl, sulfonyl, sulfinylalkylene and sulfonylalkylene, and wherein any one of the foregoing Z groups having one or more substitutable positions may be substituted with one or more of hydroxyl, alkyl, amino and alkylamino; wherein each of $R^1$ and $R^2$ is independently selected from hydrido, alkyl, aralkyl and alkylaminocarbonyl, and wherein any of the foregoing $R^1$ and $R^2$ groups having a substitutable position may be substituted with one or more substituents selected from hydroxy, alkyl, halo, haloalkyl, alkoxy, amino, aminoalkyl, alkylaminoalkyl, arylaminoalkyl ana alkylaminocarbonyl; wherein $R^1$ and $R^2$ may be taken together to form a heterocyclic group, so as to include the nitrogen atom which is attached to $R^1$ and $R^2$ of Formula I, said heterocyclic group having three to about ten ring members with one to three of said ring members being independently selected from nitrogen, oxygen and sulfur atoms and the remaining ring members being carbon atoms, with at least one of the selected hetero atoms being the nitrogen atom of Formula I which is attached to $R^1$ and $R^2$, any one of which ring members may be substituted with alkyl or aryl; and wherein $R^3$ is hydrido or is a residue of a natural or an unnatural α-amino acid, said residue consisting of the fragment attached to the α-carbon of the amino acid other than hydrido; or a pharmaceutically-acceptable salt thereof.

It is believed that the compounds defined by Formula I are novel where the Formula I definition is qualified by the following proviso descriptions: when Z is a single bond so that the b ring is a five-membered ring, then each of X, Y, $R^1$, $R^2$ and $R^3$ cannot be hydrido simultaneously; and when Z is a nitrogen atom and each of $R^1$, $R^2$ and $R^3$ is hydrido and one of X and Y is chloro, then the other of X and Y cannot be methoxy.

It is believed that novel pharmaceutical compositions, as well as novel methods of therapeutic treatment, are provided wherein a therapeutically-effective compound is selected, for inclusion in the composition or for use in the treatment, from the class of compounds defined by Formula I without qualification of Formula I with any of the foregoing proviso descriptions.

A preferred class of compounds within Formula I consists of those compounds wherein each of X and Y is independently selected from hydrido, hydroxyl, alkyl, haloalkyl, halo, alkoxy, amino and alkylamino; wherein Z is a single bond so that the b ring is a five-membered ring, or Z is a group selected from oxygen atom, sulfur atom, carbonyl, imino, sulfinyl, sulfonyl, alkylene, alkenylene, carbonylalkylene, iminoalkylene, aminoalkylene, thioalkylene, sulfinylalkylene and sulfonylalkylene, and wherein said alkylene-containing groups have one to about five carbon atoms, and wherein anyone of which Z groups having one or more substitutable positions may be substituted with one or more of hydroxyl, alkyl of one to about ten carbon atoms, amino and alkylamino having one or two alkyl portions each of one to about ten carbon atoms; wherein each of $R^1$ and $R^2$ is independently selected from hydrido, alkyl of one to about ten carbon atoms, phenylalkyl having an alkyl portion of one to about five carbon atoms and alkylaminocarbonyl having one or two N-substituted alkyl portions each of one to about ten carbon atoms, any one of which $R^1$ and $R^2$ groups having one or more substitutable positions may be substituted with one or more substituents selected from hydroxyl, alkyl, halo, haloalkyl, alkoxy, amino, aminoalkyl, alkylaminoalkyl, phenylaminoalkyl and alkylaminocarbonyl, and wherein said alkyl-containing substituents have one to about five carbon atoms; wherein $R^1$ and $R^2$ may be taken together to form a heterocyclic group, so as to include the nitrogen atom which is attached to $R^1$ and $R^2$ of Formula I, said heterocyclic group having three to about eight ring members with one or two ring members being independently selected from nitrogen, oxygen and sulfur atoms, the remainder of said ring members being methylene groups, any one of which ring members may be substituted with alkyl of one to about ten carbon atoms or phenyl; wherein $R^3$ is hydrido or is a residue of a natural or unnatural α-amino acid, said residue selected from alkyl, cycloalkyl, hydroxyalkyl, aminoalkyl, cycloalkylalkyl, alkylthioalkyl, phenyl, phenylalkyl, hydroxybenzyl, carboxyalkyl, mercaptoalkyl, carboxylalkylthioalkyl, diaminoalkyl, aminocarbonylalkyl, hydroxyhalophenylalkyl, aminohydroxyalkyl, heterocyclic, hydroxyheterocyclic, heterocyclicalkyl, aryloxyaralkyl, carboxyaminoalkylthioalkyl; or a pharmaceutically-acceptable salt thereof.

A more preferred class of compounds within Formula I consists of those compounds wherein each of X and Y is independently selected from hydrido, hydroxyl, alkyl, haloalkyl, halo, alkoxy, amino and aminoalkyl, and wherein each of said alkyl-containing groups have one to about ten carbon atoms; wherein Z is a single bond so that the b ring is a five-membered ring, or Z is a group selected from sulfur atom, sulfinyl, sulfonyl, alkylene, alkenylene of two to about four carbon atoms, thioalkylene, sulfinylalkylene and sulfonylalkylene, and wherein each of said alkylene-containing groups have one to about four carbon atoms, and wherein any one of which Z groups having one or more substitutable positions may be substituted with one or more of hydroxyl, alkyl of one to about five carbon atoms, amino and alkylamino having one or two alkyl portions each of one to about ten carbon atoms; wherein each of $R^1$ and $R^2$ is independently selected from hydrido, alkyl of one to about five carbon atoms, benzyl, phenethyl, phenpropyl, alkylaminoalkyl having one or two N-substituted alkyl portions each of one to about five carbon atoms, any one of which $R^1$ and $R^2$ groups having one or more substitutable positions may be substituted with one or more substituents selected from hydroxyl, alkyl of one to about five carbon atoms, alkoxy of one to about five carbon atoms and amino; wherein $R^1$ and $R^2$ may be taken together to form a heterocyclic group so as to include the nitrogen atom which is attached to $R^1$ and $R^2$ of Formula I, said heterocyclic group selected from pyrrolidinyl, piperidinyl, piperazinyl, morpholinyl and thiomorpholinyl, any one of which heterocyclic groups may be substituted with one or more groups selected form alkyl of one to about five carbon atoms and phenyl; wherein $R^3$ is a group selected from hydrido, methyl, ethyl, isopropyl, hydroxymethylene, hydroxyethylene, n-butylene, isobutylene, aminobutylene, carboxymethylene, carboxyethylene, mercaptomethylene, carboxymethylaminodithiomethylene, methylthioethylene, phenyl, benzyl, para-hydroxylbenzyl, imidazolyl, imidazolylmethylene, 4-[4-hydroxy-3,5-diiodo-phenoxy]-benzyl, indolyl, 3-indolylmethylene, 3-guanidinopropyl, carboxamidomethylene and carboxamidoethylene any one of which $R^3$ groups having a substitutable position may be substituted with one or more groups selected from halo, hydroxy and alkyl; or a pharmaceutically-acceptable salt thereof.

A more highly preferred class of compounds within Formula I consists of those compounds wherein each of X and Y is independently selected from hydrido, hydroxyl, methyl, ethyl, n-propyl, isopropyl, n-butyl, sec-butyl, iso-butyl, n-pentyl, iso-pentyl, neopentyl, trifluoromethyl, fluoro, chloro, methoxy, ethoxy, propoxy, amino, aminomethylene, aminoethylene and aminopropylene; wherein Z is a group selected from methylene, ethylene, propylene, ethenylene, propenylene, thiomethylene, thioethylene, thiopropylene, methylenethiomethylene and methylenethioethylene, any one of which may be substituted by hydroxyl, methyl, ethyl, n-propyl, isopropyl, amino, N-methylamino, N,N'-dimethylamino, N-ethylamino and N,N'-diethylamino; wherein each of $R^1$ and $R^2$ is independently selected from hydrido, methyl, ethyl, n-propyl, iso-propyl, n-butyl, iso-butyl, sec-butyl, n-pentyl, iso-pentyl, neopentyl, benzyl, N-methylaminomethyl, N,N'-dimethylaminomethyl, N-ethylaminomethyl and N,N'-diethylaminomethyl, any one of which may be substituted with one or more of substituents selected from hydroxyl, methyl, ethyl, n-propyl, iso-propyl, n-butyl, iso-butyl, sec-butyl, n-pentyl, iso-pentyl and neopentyl; wherein $R^1$ and $R^2$ may be taken together to form a heterocyclic group so as to include the nitrogen atom which is attached to $R^1$ and $R^2$ of Formula I, said heterocyclic group selected from pyrrolidinyl, piperazinyl, piperidinyl, morpholinyl and thiomorpholinyl, any one of which may be substituted with one or more groups selected from methyl, ethyl, n-propyl, iso-propyl, n-butyl, iso-butyl, sec-butyl, tert-butyl, n-pentyl, iso-pentyl, neopentyl and phenyl; wherein $R^3$ is hydrido or is a residue, other than hydrido, attached to the α-carbon of a natural or unnatural α-amino acid, said amino acid selected from aspartic acid, asparagine, cystine, cysteine, glutamic acid, glutamine, glycine, histidine, δ-hydroxylysine, allo-δ-hydroxylysine, isoleucine, alloisoleucine, leucine, lysine, methionine, phenylalanine, serine, threonine, allothreonine, thyroxine, tryptophan, tyrosine, dibromotyrosine, diiodotyrosine, valine, allylglycine, norvaline, norleucine, aminomalonic acid, aminoadipic acid, aminopimelic acid, pipecolinic acid, 5-hydroxypipecolinic acid, β-methyltryptophan, β-phenylserine, phenylglycine, cyclohexylglycine, cyclohexylalanine, furylalanine, thienylalanine, naphthylalanine and pyridylalanine; or a pharmaceutically-acceptable salt thereof.

A most highly preferred class of compounds within Formula I consists of those compounds wherein each of X and Y is hydrido; wherein Z is selected from methylene, ethylene, ethenylene, thiomethylene and thioethylene; wherein each of $R^1$, $R^2$ and $R^3$ is hydrido; or a pharmaceutically-acceptable salt thereof.

Compounds within Formula I of highest interest are the following:
2-(2,3-6,7-dibenzocycloheptanylamino)acetamide;
2-(2,3-6,7-dibenzocyclohept-4-enylamino)acetamide; and
2-(2,3-6,7-dibenzo-4-thiacycloheptanylamino)acetamide.

The term "hydrido" denotes a single hydrogen atom (H). The term "alkylene" embraces a methylene group, i.e., a —CH$_2$— group, or a series or chain of two or more methylene groups —CH$_2$—(CH$_2$)$_n$— wherein "n" is a whole number selected from two through about five, which chain is characterized in being divalent and containing no unsaturation, an example of which is an ethylene group (—CH$_2$CH$_2$—). The term "alkenylene" embraces moieties having two to about six carbon atoms and having a double bond between two adjacent carbon atoms with terminal carbon atoms each being monovalent, such as an ethylenyl moiety. The term "alkylidene" embraces a methenyl group, i.e., a =CH— group, or a series of hydrocarbyl groups of two to six carbons total with one terminal carbon being divalent and the other terminal carbon being monovalent, such as an ethenylidene group (=CHCH$_2$—). Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to about ten carbon atoms, such as cyclopropyl, cyclobutyl, cyclohexyl and cycloheptyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy", embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group, of one to about ten carbon atoms, attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "sulfinyl" and "sulfonyl", whether used alone or linked to other terms, denote respectively divalent radicals =SO and =SO$_2$. The term "heterocyclic" used alone or in conjunction with another term embraces ring structures having four to about nine ring members, one or two of which ring members being heteroatoms selected from oxygen, nitrogen and sulfur, and the remaining ring members being carbon atoms, which ring structure may be fully saturated, partially unsaturated or fully unsaturated, examples of such heterocyclic groups being imidazolyl, indolyl, pyrrolidinyl and thiomorpholino.

Within this class of tricyclic glycinamide compounds of the invention are the pharmaceutically-acceptable salts of the compounds of Formula I, including acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, alginic, β-hydroxybutyric, malonic, galactaric and galacturonic acid. Suitable pharmaceutically-acceptable base addition salts of compounds of Formula I include metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereomeric salts by treatment with an optically active acid or base. Examples of appropriate acids are tartaric, diacetyltartaric, dibenzoyltartaric, ditoluoyltartaric and camphorsulfonic acid. Then, the mixture of diastereomers may be resolved by crystallization followed by liberation of the optically active bases from these salts. A different process for separation of optical isomers involves the use of a chiral chromatography column optimally chosen to maximize the separation of the enantiomers. Still another available method involves synthesis of covalent diastereomeric molecules by reacting compounds of Formula I with an optically pure acid in an activated form or an optically pure isocyanate. The synthesized diastereomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt. All of these stereoisomers, optical isomers, diastereomers, as well as mixtures thereof such as racemic mixtures, are within the scope of the invention.

GENERAL SYNTHETIC PROCEDURES

Compounds within Formula I can be synthesized in accordance with the following general procedures wherein for each formula shown the substitution pattern for X, Y, Z, $R^1$ and $R^2$ and $R^3$ is defined before:

Reaction Scheme A

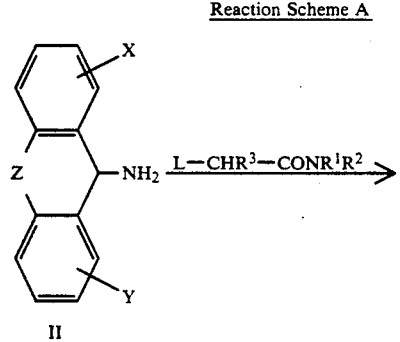

-continued
Reaction Scheme A

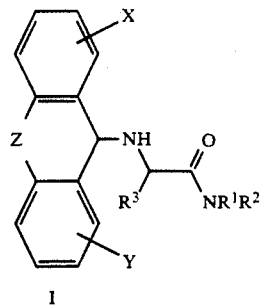

A first method which may be used to synthesize compounds of Formula I, as shown in Reaction Scheme A, involves reacting an amine of structure II with a reactant L—$CHR^3$—$CONH_2$ wherein L is a good leaving group such as a halogen, a tosyl group, a mesityl group or equivalent. The reaction is best conducted in a solvent such as an alcohol, an ether or an amide (carboxamide or phosphoramide) at a temperature between about room temperature and reflux temperature of the selected solvent in the presence of a non-nucleophilic acid quencher such as a tertiary amine or a mineral base such as sodium bicarbonate.

Reaction Scheme B

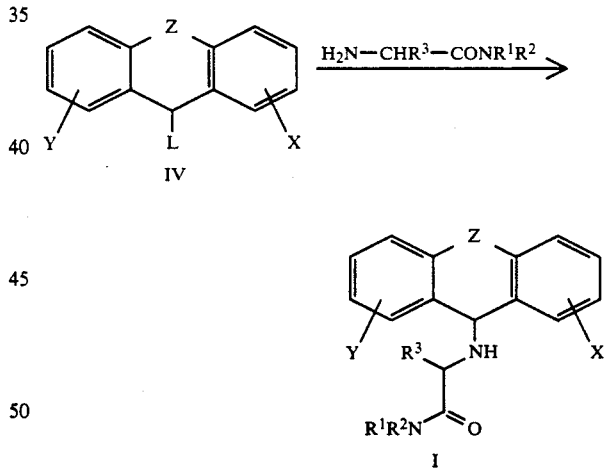

A second method which may be used to synthesize compounds of Formula I, as shown in Reaction Scheme B, involves reacting product of structure IV wherein L is a good leaving group such as a halogen, a tosyl group, a mesityl group or equivalent, with an amino amide derivative. The reaction is best conducted in a solvent such as an alcohol, an ether or an amide (carboxamide or phosphoramide) at a temperature between about room temperature and reflux temperature of the selected solvent in the presence of a non-nucleophilic acid quencher such as a tertiary amine or a mineral base such as sodium bicarbonate.

Reaction Scheme C

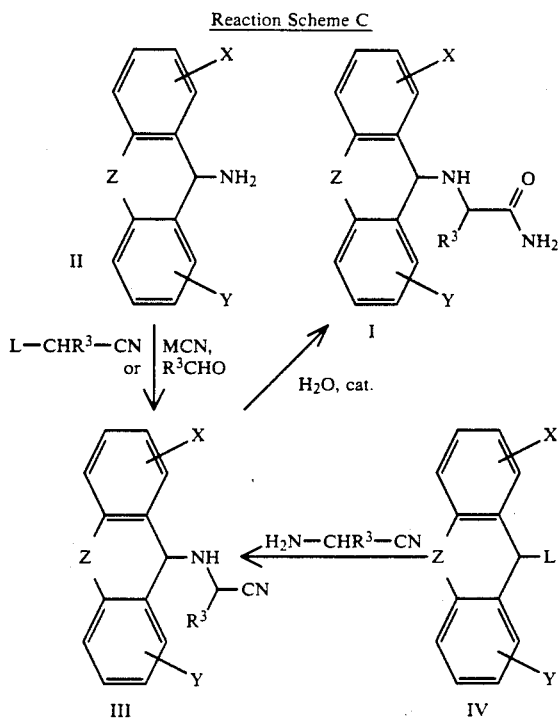

A third method which may be used to synthesize compounds of Formula I, as shown in Reaction Scheme C, involves using a precursor of an amide such as an acid, an ester or a nitrile. Amine II, in the presence of MCN where M stands for a metallic cation or other suitable cation such as a quaternary ammonium or phosphonium cation, is reacted with an aldehyde of the formula $R^3CHO$. This reaction is best conducted in water or if solubility is a problem, the reaction can be conducted in acetonitrile in the presence of aluminum oxide under ultrasound irradiation.

Reaction Scheme D

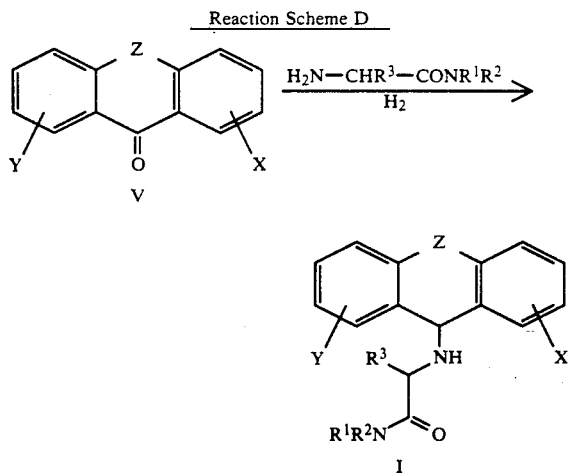

In a variation of Reaction Scheme C, derivative IV can be replaced by the corresponding ketone derivative V, as shown in Reaction Scheme D, which can react with any suitable amino acid derivative under reducing conditions such as a hydrogen atmosphere in the presence of a noble metal catalyst, or in the presence of a reducing agent such as an hydride, particularly a borohydride, to give either I or a analog of III containing the residue of the amino acid derivative involved in the reaction.

The following Examples 1-3 are detailed descriptions of the method of preparation of compounds of Formula I. These detailed preparations fall within the scope of, and serve to exemplify, the above described General Synthetic Procedures which form part of the invention. These Examples 1-3 are presented for illustrative purposes only and are not intended as a restriction on the scope of the invention. All parts are by weight unless otherwise indicated.

Example 1

2-(2,3-6,7-dibenzocycloheptanylamino)acetamide

A reaction vessel was charged with 7 g (33.5 mmole) of 2,3-6,7-dibenzocycloheptanylamine dissolved in 150 ml of ethanol. Then, a mixture of 3.13 g (33.5 mmole) of chloracetamide and 2.9 g (34 mmole) of sodium bicarbonate was added to the reaction vessel and the suspension was heated to reflux and held at reflux for 4 days. Solvent was evaporated from the mixture under reduced pressure. The residue was dissolved in water and was extracted with dichloromethane. The organic phase was dried over potassium carbonate and then the solvent was evaporated. The oily product was solidified in ether, and the solid was purified further by crystallization in a mixture of cyclohexane and ethyl acetate.

Example 2

2-(2,3-6,7-dibenzocyclohept-4-enylamino)acetamide

A reaction vessel was charged with 4 g (16 mmole) of 2,3-6,7-dibenzocyclohept-4-enylamine hydrochloride dissolved in 150 ml of isopropanol. Then, a mixture of 3 g (16 mmole) of iodoacetamide and 2.8 g (33 mmole) of sodium bicarbonate was added to the reaction vessel and the reaction mixture was heated to reflux and held at reflux for 21 hours. Solvent was evaporated from the mixture under reduced pressure. The residue was dissolved in water and was extracted with dichloromethane. The organic phase was dried over potassium carbonate and then the solvent was evaporated. The solid was dissolved in ethanol, then either-HCl was added and the precipitate which appeared was filtered. The filtered-out material was dissolved in ethanol and ether added. The solid was filtered out and stirred in 5% aqueous NaOH, then the free base was filtered out and crystallized from a mixture of ethyl acetate and pentane.

Example 3

2-(2,3-6,7-dibenzo-4-thiacycloheptanylamino)acetamide

A reaction vessel was charged with 1.95 g (8.6 mmole) of 2,3-5,6-dibenzo-4-thiacycloheptanylamine dissolved in 150 ml of isopropanol. Then, a mixture of 1.6 g (8.6 mmole) of iodoacetamide and 0.92 g (11 mmole) of sodium bicarbonate was added and the suspension was brought to reflux for 15 hours. Solvent was evaporated under reduced pressure. The residue was dissolved in dichloromethane and was washed with water. The organic phase was dried over potassium carbonate and then the solvent was evaporated. The solid was dissolved in ethanol, then ether-HCl was added and the hydrochloride salt was filtered out. The salt was crystallized twice from a mixture of ethanol and ether, dissolved in aqueous sodium bicarbonate, extracted with dichloromethane, and the organic phase was dried over potassium carbonate and evaporated under reduced pressure. The free base was crystallized twice from a mixture of ethyl acetate and pentane.

TABLE 1

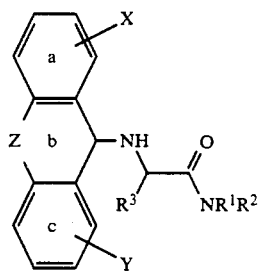

| Cpd # | X | Y | Z | $R^1$ | $R^2$ | $R^3$ | Elementary Analysis | | *M.P. °C. |
|---|---|---|---|---|---|---|---|---|---|
| | | | | | | | Calc'd. | Found | |
| 1 | H | H | —CH$_2$—CH$_2$— | H | H | H | C 76.66 | 76.51 | 125.1 |
| | | | | | | | H 6.81 | 6.82 | |
| | | | | | | | N 10.52 | 10.57 | |
| 2 | H | H | —CH=CH— | H | H | H | C 77.25 | 77.05 | 176 |
| | | | | | | | H 6.10 | 6.15 | |
| | | | | | | | N 10.60 | 10.62 | |
| 3 | H | H | —CH$_2$—S— | H | H | H | C 67.45 | 67.74 | 135 |
| | | | | | | | H 5.66 | 5.64 | |
| | | | | | | | N 9.83 | 9.81 | |

*M.P. = Melting Point

Other compounds of Formula I which can be prepared in accordance with the above-described general and specific procedures are as follows:

2-(2,3-6,7-dibenzocycloheptanylamino)acetamide;
2-(2,3-6,7-dibenzocyclohept-4-enylamino)acetamide;
2-(2,3-6,7-dibenzo-4-thiacycloheptanylamino)acetamide;
2-(2,3-6,7-dibenzo-4-oxacycloheptanylamino)acetamide;
2-(2,3-6,7-dibenzo-4-azacycloheptanylamino)acetamide;
2-(2,3-6,7-dibenzo-4-azacyclohept-4-enylamino)acetamide;
2-[2,3-6,7-(4,4'-difluorodibenzo)cycloheptanylamino]acetamide; and
2-[2,3-6,7-(3-fluorodibenzo)cycloheptanylamino]acetamide.

BIOLOGICAL EVALUATION

Treatment of a mammal afflicted by or susceptible to certain CNS disorders is accomplished by administration of a therapeutically-effective amount of a compound of Formula I. In particular, compounds 1-3 of Table 1 were evaluated by in vitro and in vivo animal model assays to determine the pharmacological properties of such compounds and their suitability for use as therapeutic drugs in humans. These biological assays, as described below, consisted of prevention of induced convulsions in mice, a TCP binding study in rat brain, determination of acute toxicity in mice and an animal behavior assay. Except as otherwise specified, the animals used in the in vivo test were male Swiss albino mice of weight 22 to 33 g [CD1, Charles River, France], housed in groups of 10 on a 12-hour dark-light cycle for at least one week and fasted overnight prior to testing.

3-Mercaptopropionic Acid Induced Convulsions

Compounds of Formula I were examined as inhibitors of convulsions and death induced by the convulsant agent 3-mercaptopropionic acid (3-MPA, 120 mg/kg subcutaneously) [W. van Dorsser, D. Barris, A. Cordi and J. Roba, Arch. Int. Pharmacodyn., 266, 239–249 (1983)]. The compounds of the invention were administered orally at a dosage of either 100 mg/kg or 30 mg/kg in a volume of 10 ml/kg each to 5 mice, at intervals of 30 minutes or 2 hours before convulsions were induced. The number of mice protected against tonic convulsions and the number of dead mice were noted. Results are given in Table II as a score which represents the total number of mice protected for two groups of 5 animals (3-MPA). Overall, Compounds #1 and #3 show very good activity as inhibitors of tonic convulsions.

TCP Binding Study

The effect of compounds of Formula I on TCP (1-[1-(2-thienyl)cyclohexyl]piperidine) binding was measured in rat brain synaptic membranes (SPM) prepared by known methods [J. B. Monahan & J. Michel; J. Neurochem., 48, 1699–1708 (1987)]. Prior to their use in the binding assay, frozen SPM were thawed, then diluted twenty fold with 50 mM Tris/acetate [pH 7.4, containing 0.04% (v/v) Triton X-100], incubated for 30 min. at 37° C. and centrifuged at 95,000 xg for 15 min. The Triton X-100 treated SPM were washed with 5 mM Tris/HCl (pH 7.4) and centrifuged a total of six times. Compound of the invention was incubated at differing concentrations with SPM (0.2–0.4 mg protein) and 2 nM tritiated TCP, in a total volume of 0.5 ml of 5 mM Tris/HCl buffer (pH 7.4) at 25° C. for 60 min. The samples were filtered through glass fiber filters (Schleicher & Schuell #32) which had been pretreated with 0.05% (v/v) polyethyleneimine, washed with 2 ml of ice-cold 5 mM Tris/HCl buffer, and then counted on a Beckman LS 5800 liquid scintillation counter with automatic corrections for quenching and counting efficiency. Inhibition of TCP binding was measured as a decrease in basal binding. Non-specific binding was defined as the residual binding in the presence of 60 mM phencyclidine. TCP binding inhibition values ($IC_{50}$) were calculated using logit-log analysis and calculations and regression analysis were performed using templates developed for Lotus 123 by known methods [L. M.

Pullan, *Computer Appli. Biosci.*, 68,113-122 (1987)]. Results are given in Table II.

Acute Toxicity

The acute toxicity was determined after oral administration of the test compound to mice. Compound to be tested was suspended in a 1% tragacanth gum mucilage and was administered by means of an intragastric probe to a group of three male mice. Doses used in the test were determined by observing toxic effects on the mice, which doses varied from 3,000 mg/kg down to about 3 mg/kg. The mortality was recorded over a period of 15 days. The $LD_{50}$ result in Table II was calculated according to published methods [Lichtfield and Wilcoxon, *J. Pharmacol. Exp. Ther.*, 96, 99 (1949)] and is expressed in mg of test compound per kilogram of mouse body weight.

Behavioral Study

Behavioral effect of compounds of the invention on animals were determined by observations taken at 5 to 6 hours and at 24 hours after administration of compounds of the invention. Determinations were made based on a method derived from that of S. Irwin [See R. A. Turner, *Screening Methods in Pharmacology*, Chapter 3, pages 22-34, Academic Press, N.Y. (1965)]. If an anomaly were noted, the observation was extended and smaller doses were tested. Possible types of behaviors to be observed are as follows: analgesia (AAG), convulsions (CON), depression (DEP), exophthalmia (EOP), excitation (EXC), hyperalgesia (HAG), hypothermia (ATH), hypotonia (ATN), piloerection (PIE), palpebral ptosis (PTO), reduction of the pinna reflex (RPI), reduction of the rearing reflex (RRE), reduction of the flexion reflex (RRF), sedation (SED), tremors (TRE), cyanosis (CYA), diarrhea (DIA), increase of the pinna reflex (HPI), increase of the flexion reflex (HRF), dyspnea (DYS). Two types of behavior observed are reported in Table II by numbers which represent the dose at which the behavior is observed.

TABLE II

| Compound # | $LD_{50}$ (mg/kg) | Behavior (mg/kg) | 3-MPA 30 min | 3-MPA 2 hrs | TCP Binding $IC_{50}$ (μm) |
|---|---|---|---|---|---|
| 1 | 780 | 300:SED | 10 | 10 | 38 |
| 2 |  | 1000:CON | 3 |  |  |
| 3 |  |  | 10 |  |  |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition ar readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Compound or a pharmaceutically acceptable salt thereof which is 2-(2,3-6,7-dibenzocycloheptanylamino)acetamide.

2. Compound or a pharmaceutically acceptable salt thereof which is 2-(2,3-6,7-dibenzocyclohept-4-enylamino)acetamide.

3. A pharmaceutical composition comprising a therapeutically-effective amount of an active compound and a pharmaceutically-acceptable carrier or diluent, wherein said active compound is 2-(2,3-6,7-dibenzocycloheptanylamino)acetamide, or a pharmaceutically acceptable salt thereof.

4. A pharmaceutical composition comprising a therapeutically-effective amount of an active compound and a pharmaceutically-acceptable carrier or diluent, wherein said active compound is 2-(2,3-6,7-dibenzocyclohept-4-enylamino)acetamide, or a pharmaceutically acceptable salt thereof.

5. A method for treating a mammal afflicted with or susceptible to a central nervous system disorder, cognitive disorder, neurodegenerative disease or neurotoxic injury, said method comprising administering a therapeutically-effective amount of 2-(2,3-6,7-dibenzocycloheptanylamino)acetamide or a pharmaceutically-acceptable salt thereof.

6. A method for treating a mammal afflicted with or susceptible to a central nervous system disorder, cognitive disorder, neurodegenerative disease or neurotoxic injury, said method comprising administering a therapeutically-effective amount of 2-(2,3-6,7-dibenzocyclohept-4-enylamino)acetamide or a pharmaceutically-acceptable salt thereof.

* * * * *